(12) United States Patent
von Daehne et al.

(10) Patent No.: US 6,177,418 B1
(45) Date of Patent: Jan. 23, 2001

(54) TETRACYCLIC TRITERPENES AS CHOLESTEROL-LOWERING AND ANTI-ATHEROSCLEROSIS AGENTS

(75) Inventors: Welf von Daehne, Rungsted Kyst; Wagn Ole Godtfredsen, Værløse, both of (DK)

(73) Assignee: Leo Pharmaceutical Products Ltd. A/S, Ballerup (DK)

( * ) Notice: Under 35 U.S.C. 154(b), the term of this patent shall be extended for 0 days.

(21) Appl. No.: 09/043,243

(22) PCT Filed: Aug. 28, 1996

(86) PCT No.: PCT/DK96/00359

§ 371 Date: Mar. 16, 1998

§ 102(e) Date: Mar. 16, 1998

(87) PCT Pub. No.: WO97/10256

PCT Pub. Date: Mar. 20, 1997

(30) Foreign Application Priority Data

Sep. 15, 1995 (GB) .................................................. 9518883

(51) Int. Cl.[7] .......................... A61K 31/56; A61K 31/58; C07J 13/00; C07J 17/00; C07J 21/00
(52) U.S. Cl. .......................... 514/182; 514/177; 514/179; 514/172; 514/173; 514/824; 540/7; 540/46; 540/76; 540/114; 552/508; 552/510; 552/530
(58) Field of Search .................... 514/177, 179, 514/182, 172, 173; 552/530, 508, 510; 540/7, 46, 114, 76

(56) References Cited

U.S. PATENT DOCUMENTS 3,334,014 * 8/1967 Godfredsen ............................ 167/65
3,598,811    8/1971 Immer et al. .
3,629,300 * 12/1971 Godfredsen ........................ 260/397.2
4,119,717 * 10/1978 Von Daehne et al. ............... 424/238

FOREIGN PATENT DOCUMENTS 58-059921 * 4/1983 (JP) .

OTHER PUBLICATIONS

Hattori et al., "3.beta.–hydroxy–4.beta.– methyl-fusida–17(20)[16,21–cis],24–diene (3,beta.–hydroxy–pro-tosta–17(20)[16,21–cis],24–diene) and a related triterpene alcohol", Tetrahedron Letters No. 13, 1969, pp. 1023–1026.*

Okuda et al., "Isolation of 3.beta.–hydroxy– 4.beta.–hydroxymethylfusida–17(20)[16,21–cis], 24–diene" Tetrahedron Letters No. 46, 1968, pp. 4769–4772.*

E. J. Corey et al, "New Mechanistic and Stereochemical Insights on the Biosynthesis of Sterols mfrom 2,3–Oxidosqualene", Journal of the American Chemical Society, vol. 113, No. 21, Oct. 9, 1991, pp. 8171–8172.

E.J. Corey et al, "Enantioselective Synthesis of a Protosterol, 3.beta.,20–Dihydroxyprotos–24–ene", Journal of the American Chemicsl Society, vol. 122, No. 17, Aug. 15, 1990, pp. 6429–6431.

H. Immer et al, "Synthese und Biologishe Auswertung von 3.beta.,20(R)–Dihydroxy–Protost–24–en", Helvetica Chimica Acta, vol. 54, No. 5, Jul. 12, 1971, pp. 1346–1360.

(List continued on next page.)

*Primary Examiner*—Barbara Badio
(74) *Attorney, Agent, or Firm*—Pillsbury Madison & Sutro LLP

(57) ABSTRACT

The invention is directed to compounds, compositions and method of preparation of compounds of formulae I and II:

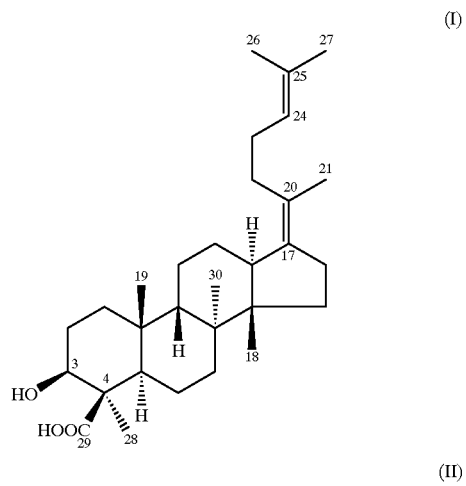

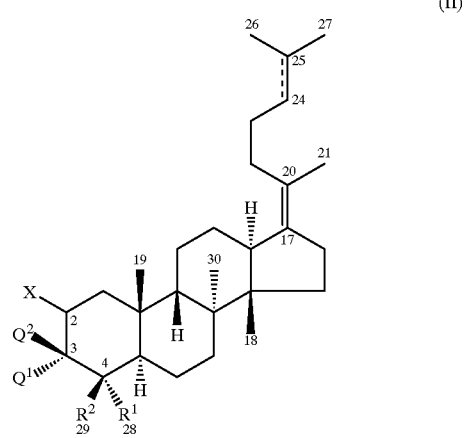

wherein X, $Q^1$, $Q^2$, $R^1$ and $R^2$ are as defined by the specification. The compounds are disclosed as useful cholesterol-lowering and anti-atherosclerosis agents.

7 Claims, No Drawings

OTHER PUBLICATIONS

H. Immer et al "Synthesis of 31–Norprotost–24–ene–3.beta.,20R–diol", Tetrahedron Letters, No. 53, 1969, pp. 4725–4728.

Tetsuyasu Hattori et al, "3.beta.–Hydroxy– 4.beta.–methyl-fusida–17(20) [16,21–cis], 24–diene (3.beta.–Hydroxy–protosta–17 (20) [16,21–cis], 24–diene and a Related Triterpene Alcohol", Tetrahedron Letters, No. 13, 1969, pp. 1023–1026.

Shigenobu Okuda et al, "Isolation of 3.beta.–Hydroxy–4.beta.–hydroxymethylfusid a–17 (20) [16,21–cis], 24–diene" Tetrahedron Letters, vol. 46, 1968, pp. 4769–4772, XP002017289.

E. J. Corey et al, "An Experimental Demonstration of the Stereochemistry of Enzymic Cyclization of 2,3–Oxidosqualene to the Protosterol System, Forerunner of Lanosterol and Cholesterol" Journal of American Chemical Society, vol. 113, No. 10, May 8,1991,pp. 4025–4026, XP002017290.

* cited by examiner

TETRACYCLIC TRITERPENES AS CHOLESTEROL-LOWERING AND ANTI-ATHEROSCLEROSIS AGENTS

This application is the national phase of international application PCT/DK96/00359 filed Aug. 28. 1996 which designated the U.S.

This invention is directed to a class of tetracyclic triterpenes, in particular protostane and fusidane (29-desmethylprotostane) derivatives, that are useful as cholesterol-lowering and anti-atherosclerosis agents.

More particularly, the invention relates to a hitherto unknown metabolite of the fungus *Fusidium coccineum* represented by the formula (I)

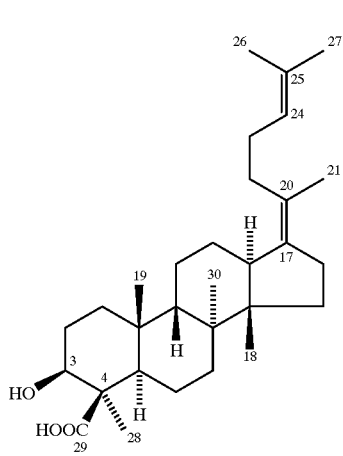

and pharmaceutically acceptable salts and in vivo hydrolysable esters thereof, and to derivatives of said compound having the general formula (II)

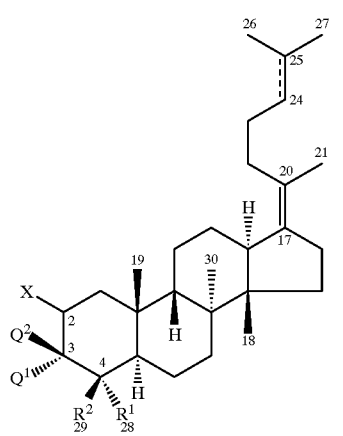

wherein $R^1$ stands for hydrogen or methyl;

$R^2$ is hydrogen, methyl, $CH_2OH$, $CH_2OR^3$, CHO, $CH=CH_2$, COOH or $COOR^4$;

$R^3$ stands for straight or branched $(C_1-C_6)$ alkyl, aralkyl or aryl, optionally substituted with halogen, hydroxy or carboxy; alkanesulfonyl or arenesulfonyl; $(C_1-C_4)$ alkanoyl or aroyl, optionally substituted with halogen, hydroxy or carboxy;

$R^4$ stands for straight or branched $(C_1-C_6)$alkyl, $(C_2-C_6)$ alkenyl, $(C_2-C_6)$alkynyl, aralkyl, aryl, alkanoyloxyalkyl or dialkylaminoethyl;

$Q^1$ and $Q^2$ are each independently hydrogen, hydroxy or a group $OR^3$; or, taken together, $Q^1$ and $Q^2$ stand for oxygen; or $Q^1$ $(Q^2)$ and $R^1$ $(R^2)$, when taken together, constitute a double bond that connects carbon atoms 3 and 4; or $Q^2$ and $R^2$, when taken together with carbon atoms 3 and 4, may form an oxetane ring.

X is hydrogen; or X and $Q^1$ $(Q^2)$, when taken together, form a double bond connecting carbon atoms 2 and 3;

the C24,25-bond is a double bond or a single bond;

and, additionally, one or more of the double bonds connecting carbon atoms 2 and 3, 3 and 4, 17 and 20, and/or 24 and 25 may optionally be epoxidized with formation of an oxirane ring or hydrated to give a carbon-carbon single bond where one of the carbon atoms is substituted with hydroxy;

with the proviso that when, at the same time, the C24, 25-bond is a double bond, $Q^1$ is hydrogen, $Q^2$ is hydroxy, and $R^1$ is methyl, then $R^2$ cannot be methyl or hydroxymethyl;

and pharmaceutically acceptable salts and in vivo hydrolysable esters thereof.

The compounds of the invention derived from the compounds of formula (II) by epoxidation or hydration can comprise several diastereomeric forms (e.cg. R and S configuration at the carbon atoms which are part of the oxirane ring or at the carbon atom bearing the hydroxy group). The invention covers all these diastereoisomers in pure form as well as mixtures thereof.

Atherosclerosis, a chronic disease related to the vascular system, is one of the most common causes of death in the Western world, and a high cholesterol level in the blood is a key risk factor in its development.

The inhibition of the biosynthesis of cholesterol constitutes an important approach to lowering serum cholesterol, and several therapeutic agents based on this principle are already available.

These agents (e.g. lovastatin, simvastatin, pravastatin and fluvastatin) interfere with an early step in the cholesterol biosynthesis—namely the conversion of hydroxymethylglutaryl-CoA (HMG-COA) to mevalonate (cf.Scheme A).

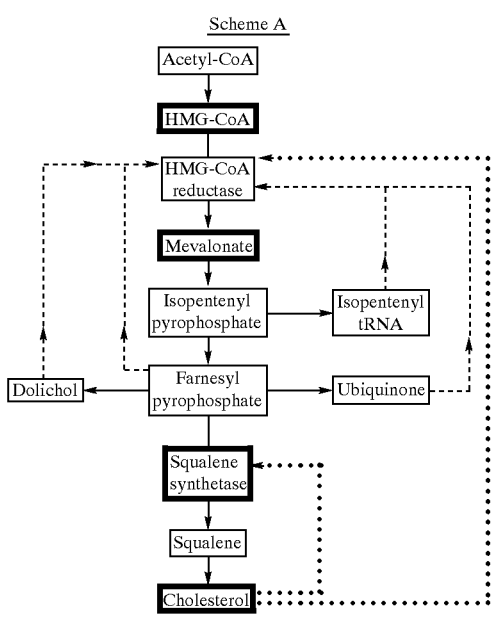

Scheme A

Scheme A is a schematic presentation of multivalent feedback regulation of HMG-CoA-reductase. The dashed lines indicate probable nonsterol regulators and the dotted lines indicate regulation by cholesterol which is derived from LDL uptake. This cholesterol suppresses HMG-CoA reductase and to a limited extent squalene synthetase (Brown & Goldstein, 1980, J. Lipid Research 21, 505–517).

However, mevalonate is also the obligate precursor of a number of non-steroidal isoprenoids such as dolichol, ubiquinone and isopentenyl t-RNA and the formation of these essential compounds will therefore also be inhibited by inhibitors of HMG-CoA reductase. This is an undesired effect and efforts have therefore been concentrated on the finding of cholesterol lowering compounds that interfere with a later step in the biosynthesis of cholesterol.

Recently, the isolation and characterisation of two new families of compounds, called squalestatins and zaragozic acids, respectively, have been reported. These compounds are potent inhibitors of the enzyme squalene synthetase (cf. Scheme A) and therefore lower the formation of the cholesterol-precursor squalene without interfering with the production of non-steroidal isoprenoids.

The conversion of 2,3-oxidosqualene into lanosterol— another intermediate in the biosynthesis of cholesterol—is another target for inhibition. This conversion, which is catalyzed by the enzyme oxidosqualene cyclase, is believed to take place as outlined in scheme B.

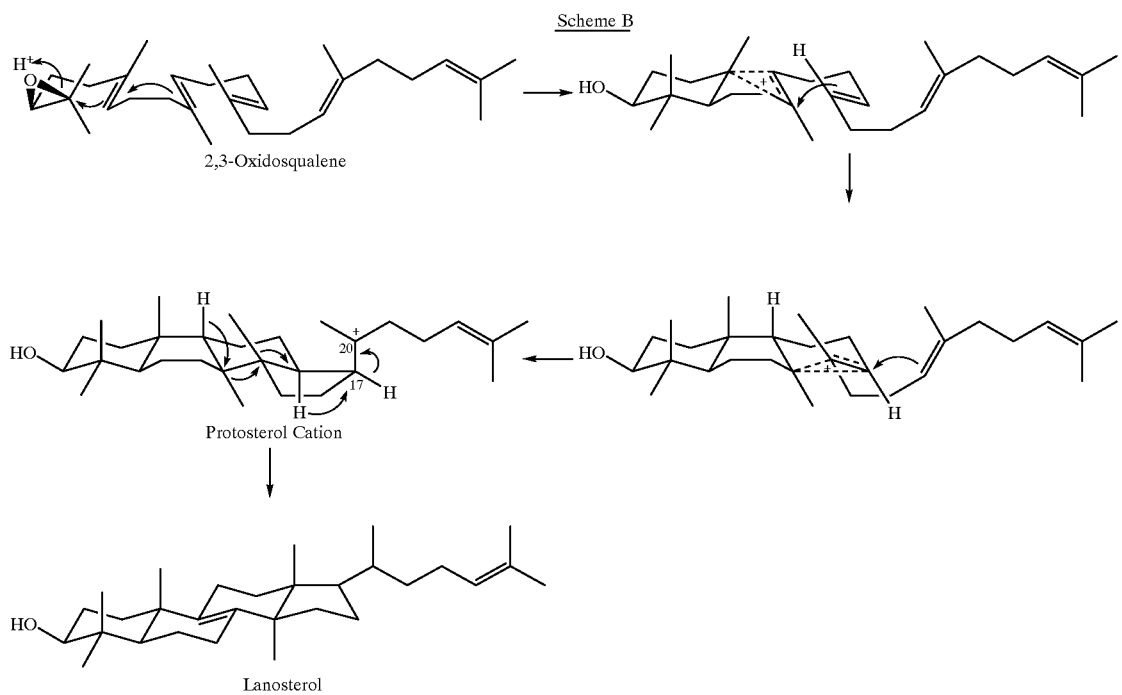

Scheme B

The 2,3-oxidosqualene, formed by enzymatic epoxidation of squalene, is folded in a pre-chair-boat-chair-boat conformation and the proton initiated cyclization proceeds through a series of rigidly-held carbocationic intermediates. The intermediate C-20 protosterol cation then undergoes backbone rearrangement to yield lanosterol.

Because of the similarity between the conformation of the protosterol cation and that of a protosterol (e.g. compound 6, Scheme 1) we hypothesized that certain compounds containing the protostane ring system might act as inhibitors of oxidosqualene cyclase and thereby inhibit the formation of cholesterol in a very specific way.

The effect of the compounds of the invention on cholesterol synthesis ($^{14}$C-acetate incorporation into cholesterol, separated by TLC) in human Hep G2 cells can be tested in vitro according to the method described by A. Boogards et al, (Biochem. J., 1987, 241, 345–351).

The effect of the compounds of the invention on cholesterol biosynthesis from [$^{14}$C]acetate or [$^3$H]mevalonate by isolated rat heptocytes and by rat or mouse liver in vivo can be tested according to the method described by Y. Tsujita et al. (Biochem. Biophys. Acta, 1986, 877, 50–60).

Two of the compounds represented by the general formula (II), i.e. those in which the C24,25-bond is a double bond, $Q^1$ is hydrogen, $Q^2$ is hydroxy, $R^1$ is methyl and $R^2$ stands for either methyl or hydroxymethyl have been described previously. (S. Okuda et al., Tetrahedron Letters 1968, 4769–4772; T. Hattori et al., Tetrahedron Letters 1969, 1023–1026; G. Visconti, Ph.D. Thesis No. 4156, ETH Zurich, 1968). Both compounds have been isolated in small amounts from the mycelium of the helvolic acid-producing fungus *Cephalosporium caerulens* and, independently, from the mycelium of *Fusidium coccineum*, the fungus known to produce fusidic acid, but an investigation of their biological activities has never been reported.

However, the discovery and recent isolation in substantial amounts of the compound of formula (I) offered the possibility to prepare larger amounts of said two compounds of formula (II) by chemical means and to study their biological activities.

It has now been found that said two compounds of formula (II) and other compounds of the present invention show activity as inhibitors of hepatic cholesterol synthesis in vitro and in vivo.

The invention also relates to methods of preparing the compounds of the formulae (I) and (II) as defined above.

The compound of formula (I) is a hitherto unknown metabolite of the fungus *Fusidium coccineum*, formed during the fermentation process in addition to fusidic acid, and can be isolated in substantial amounts by fractionation of mother liquors from which fusidic acid has been recovered.

It is noteworthy in this context that the production of fusidic acid by fermentation of *Fusidium coccineum* has been described in detail (see Biotechnology of Industrial Antibiotics, E. J. Vandamme, ed.; Marcel Dekker, Inc., New York, 1984, 427–449, and references cited therein).

The new compound is a tetracyclic triterpenoid acid $C_{30}H_{48}O_3$, containing a secondary hydroxyl group and two isolated double bonds, one trisubstituted, the other tetrasubstituted. Chemical and spectral data obtained for this compound were in agreement with the structure shown in formula (I). The compound can be used as such or in the form of salts or in vivo hydrolysable esters.

The compounds of formula (II) may conveniently be prepared from the compound of formula (I) by the routes outlined in Schemes 1 to 5. The conversion of a C24,25 double bond into a C24,25 single bond is readily performed by hydrogenolysis in the presence o: a palladium catalyst. The compounds of formula (II) wherein $R^2$ is COOH can be used as such or in the form of salts or in vivo hydrolysable esters.

The salts of the compounds are especially the pharmaceutically acceptable, non-toxic salts, such as alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)-amine or tri-(2-hydroxyethyl)-amine, cycloalkylamines, for example dicyclohexylamine, or benzylamines, for example N,N'-dibenzylethylendiamine, and dibenzylamine.

The in vivo hydrolysable esters can e.g. be alkanoyloxyalkyl, aralkanoyloxyalkyl, aroyloxyalkyl esters, such as actoxymethyl, pivaloyloxymethyl, benzayloxymethyl esters, and the corresponding 1'-oxyethyl derivatives, or alkoxycarbonyloxyalkyl esters, such as methoxycarbonyloxymethyl, ethoxycarbonyloxymethyl esters, and th.e corresponding 1'-oxyethyl derivatives, or lactonyl esters, such as phthalidyl esters, or dialkylaminoalkyl esters, such as diethylaminoethyl esters.

Scheme 1
Synthesis of compounds of formula (II) where $R^1$ is methyl and $R^2$ is methyl or hydroxymethyl

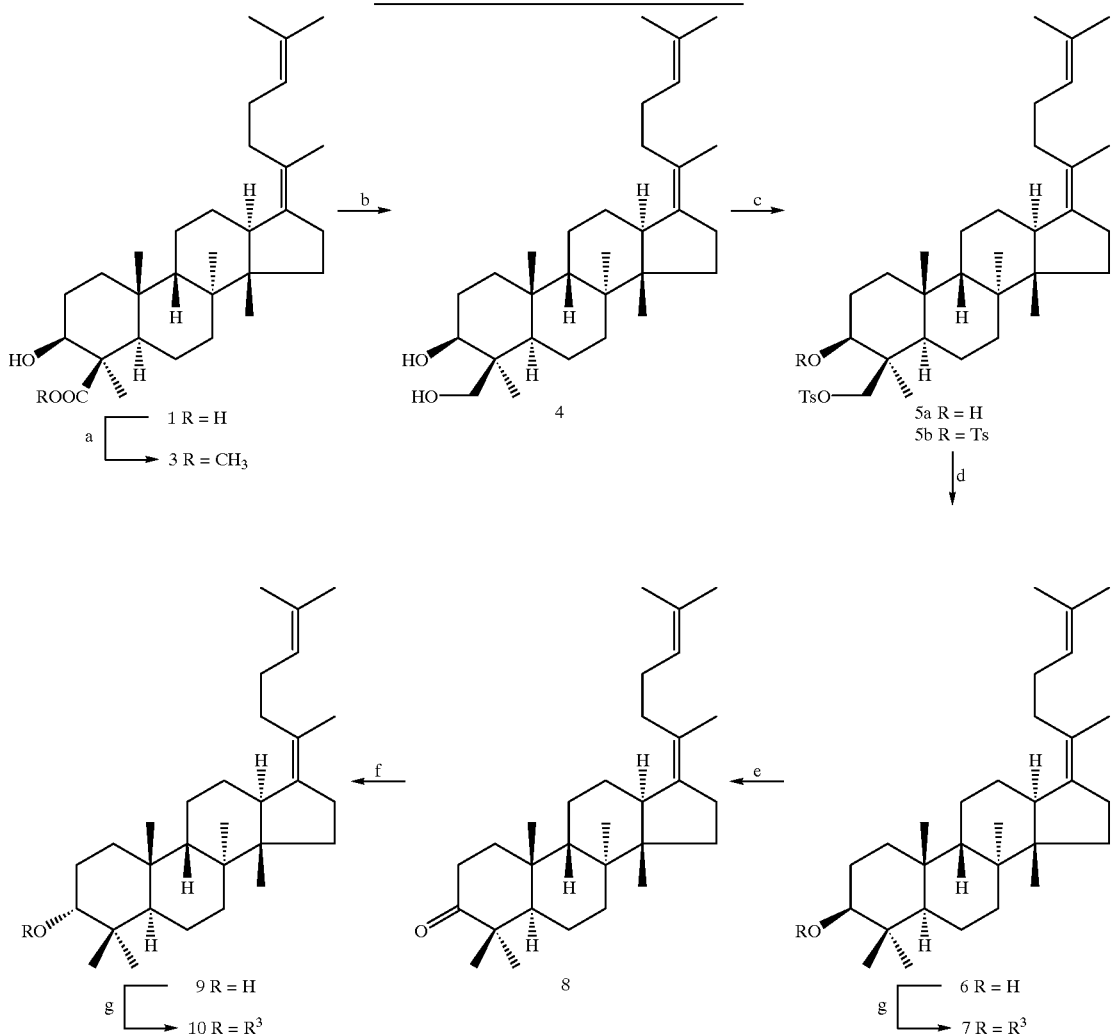

Notes to Scheme 1 a) Esterification with methyl iodide in the presence of base (e.g. potassium carbonate).
b) Reduction (e.g. with lithium FLluminium hydride).
c) Tosylation with p-toluenesulfonyl chloride in the presence of base (e.g. pyridine).
d) Reduction (e.g. with lithium ailuminium hydride).
e) Oxydation (e.g. with Jones reagent).
f) Reduction (e.g. with potassium selectride).
g) Alkylation, acylation etc.

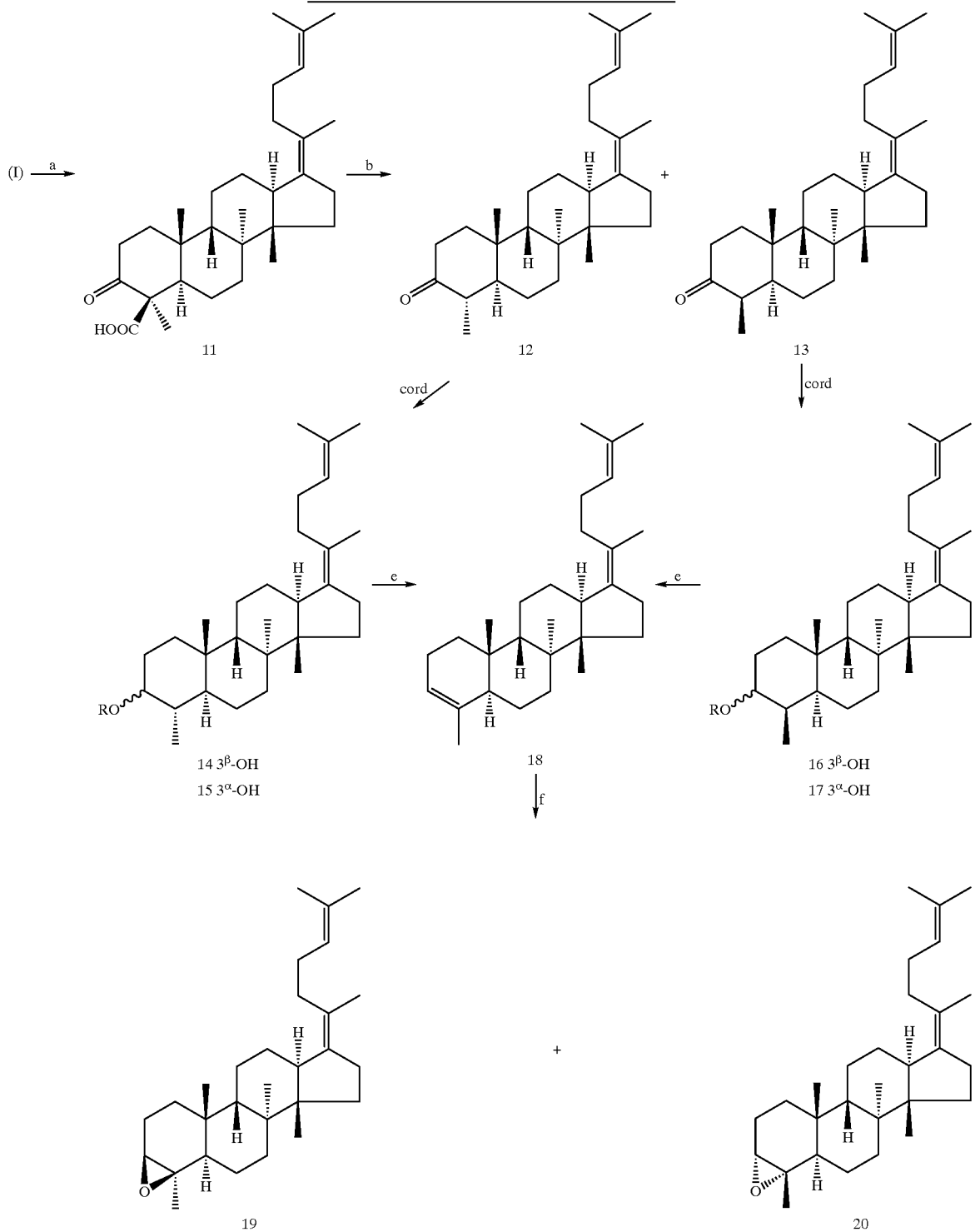

Notes to Scheme 2
a) Oxidation (e.g. with Jones reagent).
b) Decarboxylaton of β-keto acid (e.g. by thermolysis in 95% ethanol).
c) Reduction (e.g. with sodium borohydride).
d) Reduction (e.g. with potassium selectride)
e) Elimination (e.g. via tosylate in the presence of base).
f) Epoxidation (e.g. with m-chloroperbenzoic acid).

Scheme 3
Synthesis of ring A- modified compounds of formula (II) where $R^1$ is methyl by reduction/elimination of sufonates

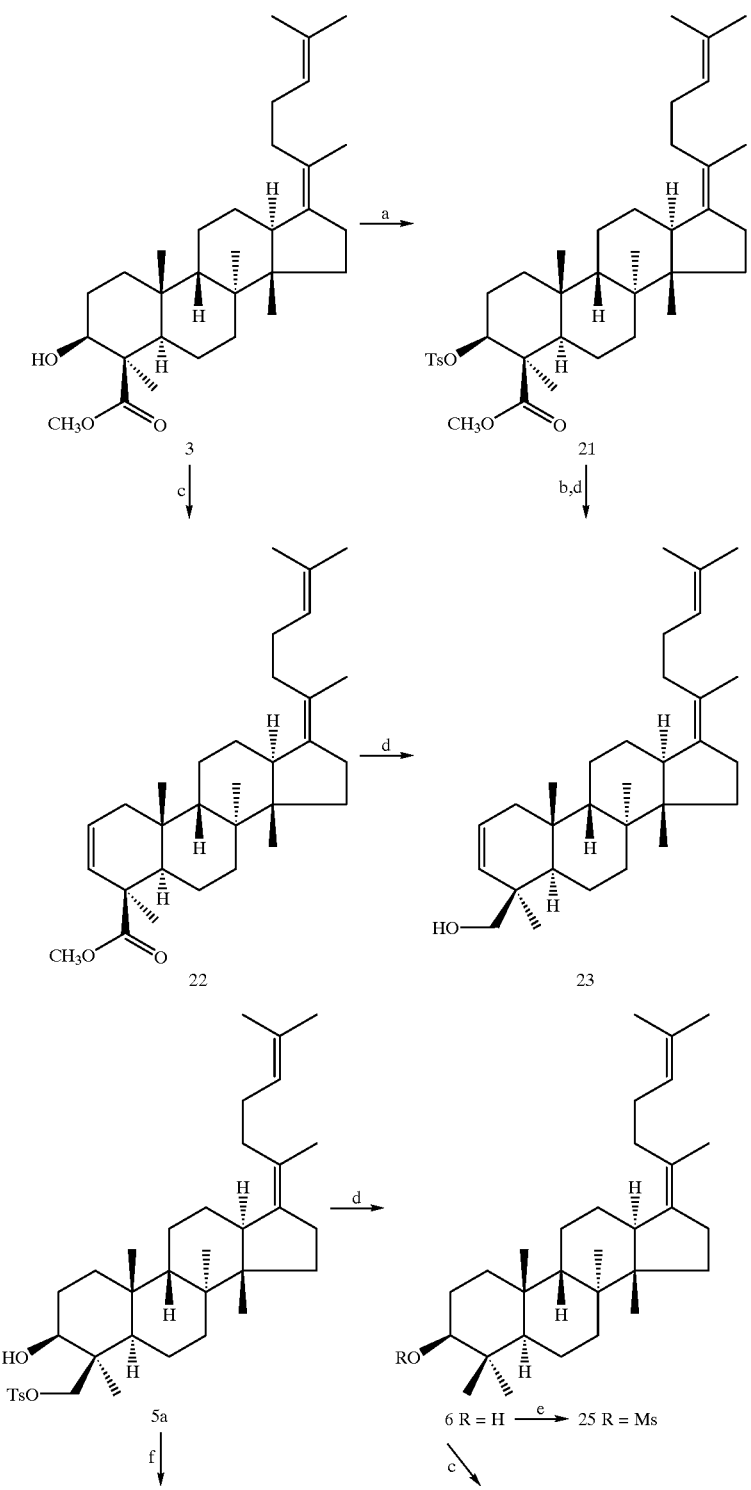

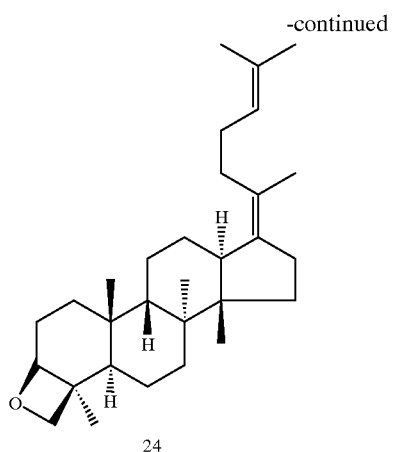

24

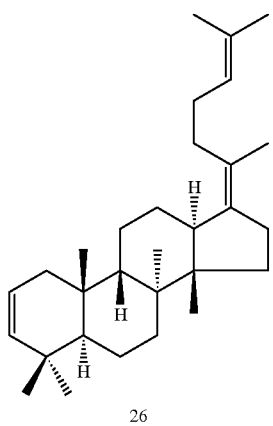

26

Notes to Scheme 3
a) Tosylation with p-toluenesulfonyl chloride in the presence of base (e.g. pyridine).
b) Elimination of p-toluenesulfonic acid (e.g. with lithium aluminium hydride).
c) Sulfonation/elimination (e.g. with triflic anhydride in pyridine).
d) Reduction (e.g. with lithium aluminium hydride).
e) Mesylation with methanesulfonyl chloride in the presence of base (e.g. pyridine).
f) Treatment with lithium triethylhydroborate ("Superhydride").

Scheme 4
Synthesis of compounds of the invention by epoxidation of compounds of formula (II) having C17 (20) and C24, 25 double bonds followed by reduction or rearrangement

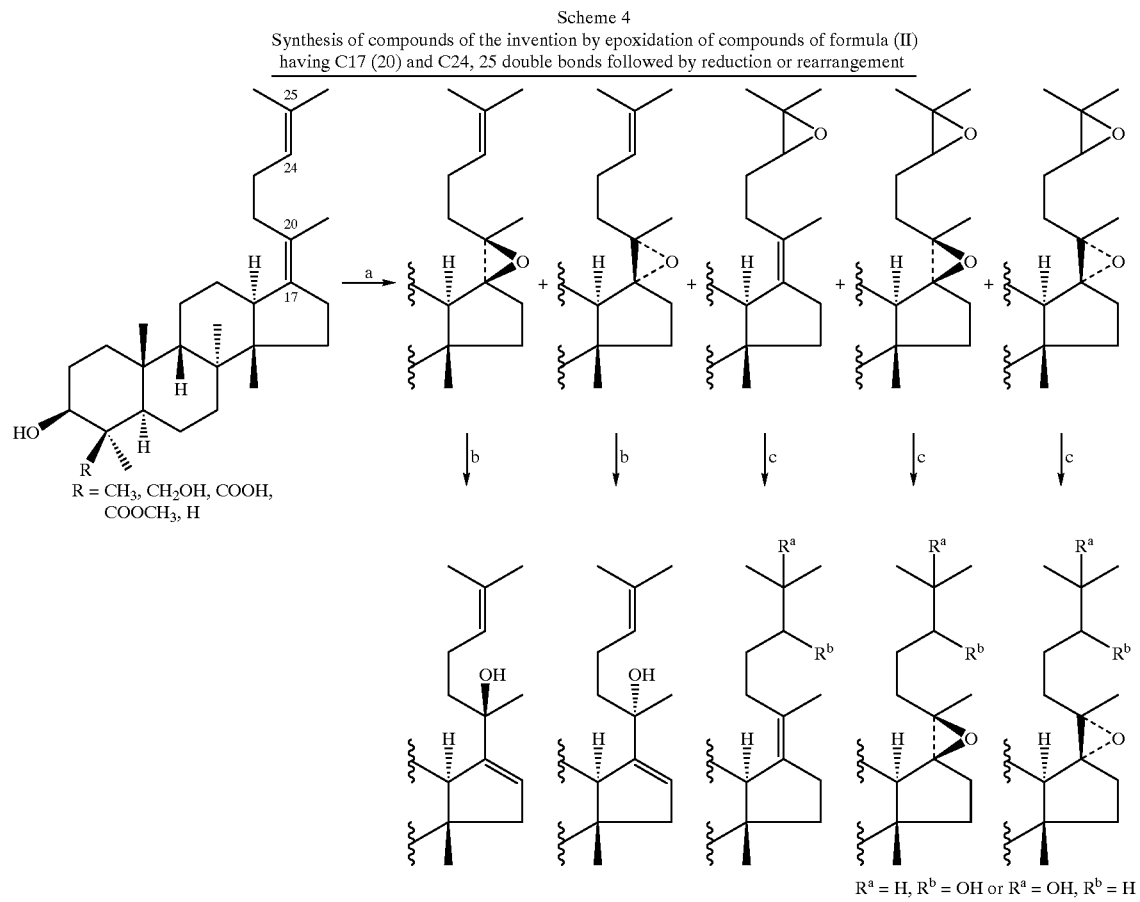

Notes to Scheme 4
a) Epoxidation (e.g. with m-chloroperbenzoic acid).
b) Rearrangement (e.g. with aluminium chloride as catalyst).
c) Reduction (e.g. with lithium aluminium hydride).

Scheme 5
Synthesis of compounds of the invention by hydroboration/oxidation or oxymercuration/demercuration of compounds of formula II having C17(20) and C24,25 double bonds

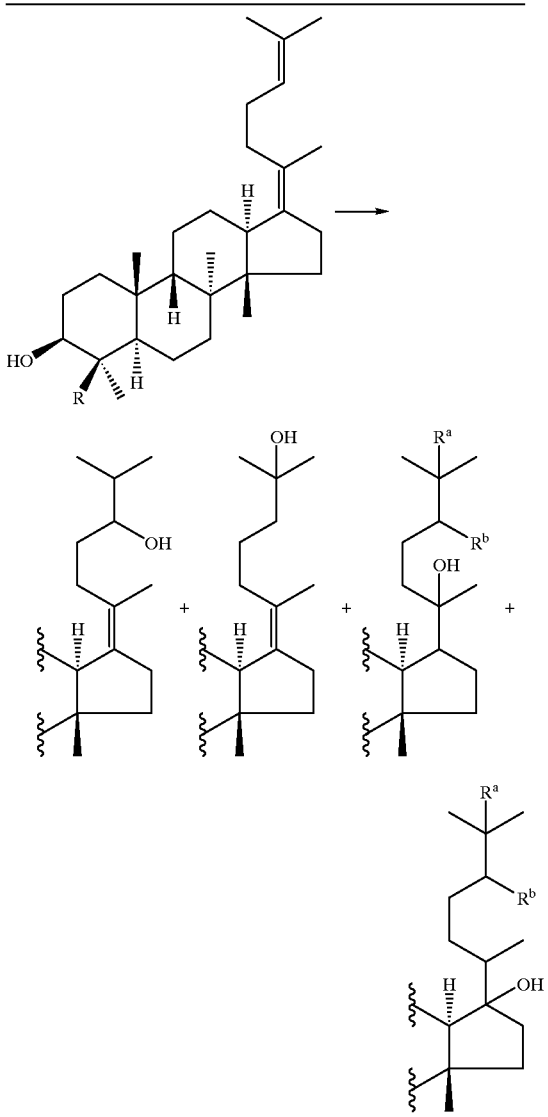

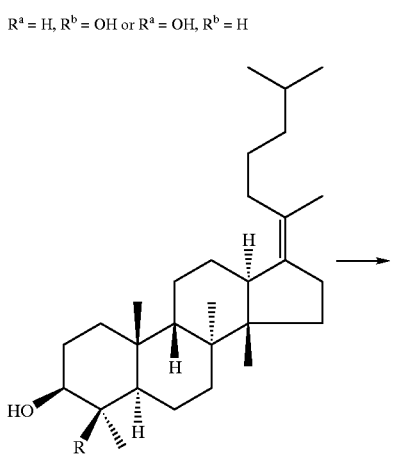

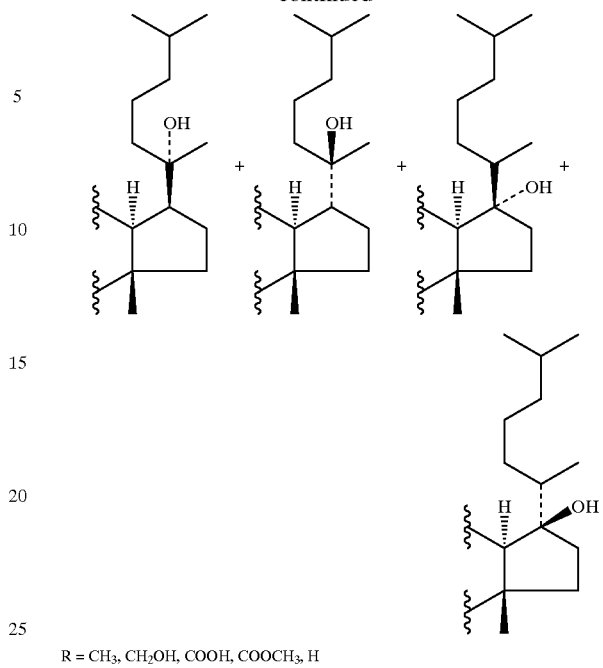

R = CH₃, CH₂OH, COOH, COOCH₃, H

Notes to Scheme 5

Hydroboration (e.g. with borane, monoalkylboranes, dialkylboranes or catecholborane) followed by oxidation (e.g. with 30% hydrogen peroxide/sodium hydroxide).

Oxymercuration (e.g. with mercury(II)acetate or trifluoroacetate) followed by demercuration (e.g. reduction with sodium borohydride or sodium trimethoxyborohydride).

It is a further object of the present invention to provide pharmaceutical compositions of (I) and (II) which are useful in the treatment of the above mentioned diseases.

The amount required of a compound of formula (I) or (II) (hereinafter referred to as the active ingredient) for therapeutic effect will, of course, vary both with the particular compound, the route of administration and the mammal under treatment. A suitable daily dose of a compound of formula (I) for systemic treatment is3 0.05 to 20 mg per kilogram mammal bodyweight, a more preferred daily dosage being 0.1 to 7 mg per kg of mammal bodyweight administered in one or more doses.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations for human medical use of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for enteral, parenteral (including subcutaneous, intramuscular, intravenous and intraperitoneal) administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus.

A tablet may be made by compressing or moulding the active ingredient optionally with one or more accessory ingredient. Compressed tablets may be prepared by compressing, in a suitable machine, the active ingredient in a free-flowing form, such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations suitable for rectal administration may be in the form of suppositories.

Formulations suitable for parenteral administration conveniently comprise a sterile oily or aqueous preparation of the active ingredient which is preferably isotonic with the blood of the recipient.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including antioxidants), emulsifying agents and the like.

The compositions may further contain other therapeutically active compounds usually applied in the treatment of the above-mentioned pathological conditions.

According to the invention, the present compounds are administered to a patient suffering from one of the above mentioned pathological conditions in a daily dose (for adults) from 3.5 mg to 1400 mg, preferably from 10–500 mg.

The invention will now be further described in the following Examples:

General

For nuclear magnetic resonance spectra (300 Mhz) chemical shift values ($\delta$) are quoted for deuteriochloroform solutions relative to internal tetramethylsilane ($\delta$=0) or chloroform ($\delta$=7.25). The value for a multiplet, either defined (doublet (d), triplet (t), quartet (q)) or not (m) at the approximate mid point is given unless a range is quoted (s=singlet, b=broad). Coupling constants (J) are given in Hertz, and are sometimes approximated to the nearest unit. Electron ionization mass spectrometry (EIMS) was used to determine molecular weights, $M^+$ corresponding to the molecular ion.

Ether is diethyl ether, and was dried over sodium. THF was dried over sodium/benzophenone. Petroleum ether refers to the pentane fraction. Reactions were run at room temperature unless otherwise noted. The work-up procedure referred to involves dilution with the specified solvent (otherwise the organic reaction solvent), extraction with water and then brine, drying over anhydrous $MgSO_4$, and concentration in vacuo to give a residue.

EXAMPLE 1

3β-Hydroxyprotosta-17(20)Z,24-dien-29-oic Acid (I)

Crude fusidic acid methanol solvate (200 g) containing 12.6% of the title compound, as determined by HPLC analysis, was dissolved in ethyl acetate (2.5 liter) at 40° C. Addition of dicyclohexylamine (100 ml) to the stirred solution caused precipitation of a white crystalline product. After stirring for 30 minutes at room temperature, the crystals were filtered off, washed with ethyl acetate, followed by petroleum ether, and dried to afford 207.5 g of dicyclohexylammonium fusidate, $C_{30}H_{48}O_6$, $C_{12}H_{23}N$.

The mother liquor was concentrated to about 500 ml, water (250 ml) was added, and the apparent pH of the mixture was adjusted to 3 with concentrated sulfuric acid.

The organic phase was separated, washed with water (2×100 ml), dried ($MgSO_4$) and evaporated. The residual oil (54.2 g) was crystallized from methanol to give 26.0 g of the title compound which according to TLC contained traces of fusidic acid. Recrystallization from acetone afforded 21.2 g of the pure compound, mp 179–180° C., $[\alpha]_D^{20}$+38.2° (cl, $CHCl_3$)

Anal. Calculated for $C_{30}H_{48}O_3$:C, 78.90; H, 10.59. Found: C, 79.01; H, 10.64.

$^1H$ NMR $\delta$ 0.77 (s,3H), 0.90 (s,3H), 1.12 (s,3H), 1.45 (s,3H),1.10–1.65 (m,12H), 1.58 (s,3H), 1.60 (s,3H), 1.68 (s,3H),1.75–2.20 (m,12H), 2.25 (dd,1H), 3.17 (dd,1H), 5.10 (bt,1H)

EXAMPLE 2

Methyl 3β-hydroxyprotosta-17(20)Z,24-dien-29-oate

To a stirred solution of 30-hydroxyprotosta-17(20)Z,24-dien-29-oic acid (45.7 g, 100 mmol) in dimethylformamide (250 ml) was added potassium carbonate (20.7 g, 150 mmol) and methyl iodide (10 ml, 150 mmol). The reaction mixture was stirred at room temperature overnight, insoluble material was removed by filtration, and the filtrate was transferred to a separating funnel with ethyl acetate (500 ml), washed with water (2×250 ml, 2×125 ml), dried ($MgSO_4$) and evaporated. The residual oil was crystallized from ether-methanol to give 43.4 g (92.2%) of the title compound, mp 99–100° C.

Anal. Calculated for $C_{31}H_{50}O_3$: C, 79.10; H, 10.71. Found: C, 79.19; H, 10.77.

$^1H$ NMR $\delta$ 0.77 (s,3H), 0.79 (s, 3H), 1.12 (s,3H), 1.39 (s,3H),1.10–1.60 (m,12H), 1.58 (bs,3H), 1.60 (s,3H), 1.68 (s,3H),1.75–2.35 (m,12H), 3.10 (m,1H), 3.65 (s,3H), 5.10 (bt, 1H)

EXAMPLE 3

3β,29-Dihydroxyprotosta-17(20)Z,24-diene

In a 3-necked round-bottom 250 ul-flask, equipped with a reflux condenser, a dropping funnel and a thermometer, lithium aluminium hydride (1.52 g, 40 mmol) was dissolved in dry ether (40 ml), and a solution of methyl 3p-hydroxyprotosta-17(20)Z,24-dien-29-oate (9.80 g, 20 mmol) in dry ether (40 ml) was added dropwise with stirring over 15 minutes. After stirring for a further 15 minutes, excess lithium aluminium hydride was removed by dropwise addition of ethyl acetate (40 ml) followed by 2N sulfuric acid (40 ml).

The mixture was filtered through a celite pad, washed with ethyl acetate (2×10 ml), and the filtrate was transferred to a separating funnel. The aqueous layer was extracted with ethyl acetate (20 ml), and the combined organic phases were washed with water (2×10 ml) and brine (10 ml), dried (MgSO$_4$) and evaporated. The residue thus obtained was crystallized from ether to afford 8.15 g (92.1) of the title compound, mp 139–140° C.

Anal. Calculated for C$_{30}$H$_{50}$O$_2$: C, 81.39; H, 11.38. Found: C, 81.52; H, 11.47

$^1$H NMR δ 0.74 (s,3H), 0.89 (s,3H), 1.12 (s,3H), 1.22 s,3H), 1.57 (bs,3H), 1.60 (s,3H), 1.68 (s,3H), 1.10–2.35 (m,23H), 2.68 (d,1H), 2.73 (d,1H), 3.29 (dd,1H), 3.34 (m,1H), 4.22 (d,1H), 5.10 (bt,1H)

EXAMPLE 4
29-Mono- and 3β-,29-Ditosylate of 3β,29-Dihydroxyorotosta-17(20)Z,24-diene To a stirred solution of 3β,29-dihydroxyprotosta-17(20) Z,24-diene (8.86 g, 20 mmol) in pyridine (50 ml) was added at 0° C. p-toluenesulfonyl chloride (7.62 g, 40 mmol) in one portion. The reaction mixture was stirred at 0–5° C. for 2 hours and then kept in a refrigerator overnight. The yellowish mixture was poured onto ice-water (200 ml) and extracted with ethyl acetate (2×100 ml). The combined organic phases were washed with 4N hydrochloric acid (200 ml), water (2×25 ml) and brine (20 ml), dried (MgSO$_4$) and evaporated to yield 12.6 g of an approximate 3:1 mixture of the mono and the ditosylate, respectively, as a foam.

A. 3β,29-Dihydroxyprotosta-17(20)Z,24-diene 3β,29-Ditosylate

The above mixture was separated by column chromatography on silicagel. Elution with 25i ethyl acetate in petroleum ether followed by evaporation and crystallization (ether) gave 2.86 g (19.0%) of the 39,29-ditosylate, mp 135–136° C.

Anal. Calculated for C$_{44}$H$_{62}$O$_6$S$_2$: C, 70.36; H, 8.32; S, 8.54. Found: C, 70.40; H, 8.35; S. 8.59.

$^1$H NMR δ 0.73 (s,3H), 0.83 (s,3H), 0.88 (s,3H), 1.08 (s,3H), 1.57 (s,3H), 1.59 (s,3H), 1.68 (s,3H), 1.10–2.30 (m,23H), 2.45 (s,3H), 2.46 (s,3H), 3.88 (d,1H), 4.21 (d,1H), 4.27 (m,1H), 5.09 (m,1H), 7.33 (m,4H), 7.74 (m,4H)

B. 3β,29-Dihydroxyorotosta-17(20)Z,24-diene 29-Monotosylate

Subsequent elution of the column with 50% ethyl acetate in petroleum ether afforded, after evaporation and crystallization (ether), 7.60 g (63.6%) of the 29-monotosylate, mp 147–148° C.

Anal. Calculated for C$_{37}$H$_{56}$O$_4$S: C, 74.45; H, 9.46; S, 5.37. Found: C, 74.44; H, 9.43; S 5.34.

$^1$H NMR δ 0.74 (s,3H), 0.87 (s,3H), 1.08 (s,3H), 1.09 (s,3H), 1.58 (s,3H), 1.60 (s,3H), 1.68 (s,3H), 1.05–1.75 (m,15H),1.85–2.35 (m,9H), 2.44 (s,3H), 3.32 (m,1H), 4.15 (ABq,2H), 5.10 (m,1H), 7.34 (d,2H), 7.78 (d,2H)

EXAMPLE 5
3β-Hydroxyprotosta-17(20)Z,24-diene

In a 3-necked round-bottom 250 ml-flask, equipped with a reflux condenser, a dropping funnel and a thermometer, lithium aluminium hydride (0.95 g, 25 mmol) was dissolved in dry ether (75 ml), and a solution of 3,29-dihydroxyprotosta-17(20)Z,24-diene 29-tosylate (2.98 g, 5 =mmol) in dry tetrahydrofurane (25 ml) was added dropwise with stirring. After the addition was finished (15 minutes), the mixture was stirred at room temperature for a further 30 minutes and then refluxed for one hour. Excess reagent was removed by dropwise addition of ethyl acetate (40 ml) followed by 2N sulfuric acid (40 ml). After filtration through a celite pad, the filtrate was transferred to a separating funnel. The aqueous layer was extracted with ethyl acetate, and the combined organic phases were washed with water (3×10 ml) and brine (10 ml), dried (MgSO$_4$) and evaporated. The resulting gum was crystallized from ether-hexane to give 2.06 g (96.6%) of the title compound, mp 97–98° C.

Anal. Calculated for C$_{30}$H$_{50}$O: C, 84.44; H, 11.81. Found: C, 83.97; H, 11.98.

$^1$H NMR δ 0.75 (s,3H), 0.79 (s,3H), 0.85 (m,1H), 0.93 (s,3H), 0.98 (s,3H), 1.13 (s,3H), 1.10–1.75 (m,14H), 1.58 (s,3H), 1.61 (s,3H), 1.68 (s,3H), 1.90–2.35 (m,9H), 3.24 (dd,1H), 5.11 (m,1H)

EXAMPLE 6
3-Oxoprotosta-17(20)Z,24-dien-29-oic Acid

To a stirred solution of 3g-hydroxyprotosta-17(20)Z,24-dien-29-oic acid (13.70 g, 30 mmol) in acetone (420 ml) was added dropwise at 0-5° C. Jones reagent (13.5 ml). After the addition was finished (about 20 minutes), the cooling bath was removed, and the reaction mixture was transferred to a separating funnel. Water (600 ml) was added, and the mixture was extracted with ether (1×500 ml, 1×250 ml). The combined organic phases were washed with water (3 x 100 ml), dried (MgSO4), and evaporated to give 12.76 g (93.5%) of the title compound as a foam which was used in the next.step without further purification (see Example 7).

$^1$H NMR δ 0.79 (s,3H), 1.08 (s,3H), 1.09 (s,3H), 1.43 (s,3H), 1.58 (s,3H), 1.60 (s,3H), 1.68 (s,3H), 1.00–2.38 (m,21H), 2.52 (m,1H), 2.80 (m,1H), 5.11 (m,1H)

EXAMPLE 7
3-Oxofusida-17(20)Z,24-diene and 4-epi-3-oxofusida-17 (20) Z, 24-diene A solution of crude 3-oxoprotosta-17(20)Z,24-dien-29-oic acid (4.32 g, 9.5 mmol) in 95% ethanol (100 ml) was refluxed for 2 hours. After cooling to room temperature, the reaction mixture was evaporated to give 3.88 g of a gum which consisted of two compounds, as revealed by TLC. These could be separated by column chromatography on silica gel eluting with 5% and 10% ether in petroleum ether.

A. 3-Oxofusida-17(20)Z,24-diene

Elution of the less polar minor compound followed, by evaporation and crystallization from ether-methanol, gave pure 3-oxofusida-17(20)Z,24-diene, mp 91–92° C., [a]$_D^{20}$+ 56.60 (c0.5, CHCl$_3$).

Anal. Calculated for C$_{29}$H$_{46}$O: C, 84.81; H, 11.29. Found: C, 84.67; H, 11.27.

$^1$H NMR δ 0.78 (s,3H), 1.01 (s,3H), 1.02 (d,3H), 1.10 (s,3H), 1.59 (s,3H), 1.61 (s,3H), 1.69 (s,3H), 0.95–1.78 (m,12H), 1.85 (m,1H), 1.90–2.36 (m,9H), 2.43 (m,2H), 5.11 (m,1H)

B. 4-Epi-3-oxofusida-17(20)Z,24-diene

Evaporation of the eluate containing the more polar major compound, followed by crystallization of the resulting gum from ether-methanol, afforded pure 4-epi-3-oxofusida-17 (20)Z,24-diene, mp 67–68° C., [a]$_D^{20}$+93.0° (c0.5, CHCl$_3$)

Anal. Calculated for C$_{29}$H$_{46}$O: C, 84.81; H, 11.29. Found: C, 84.25; H, 11.24.

$^1$H NMR δ 0.79 (s,3H), 0.81 (s,3H), 1.10 (d,3H), 1.17 (s,3H), 1.59 (bs,3H), 1.60 (s,3H), 1.68 (s,3H), 1.00–1.75 (m,10H), 1.90–2.67 (m,14H), 5.11 (m,1H)

EXAMPLE 8
3-Oxofusida-17(20)Z 24-diene

To a solution of 4-epi-3-oxofusida-17(20)Z,24-diene (2.67 g, 6.5 mmol) in tetrahydrofuran (35 ml) was added 1N methanolic potassium hydroxide (13 ml), and the mixture was kept at room temperature overnight. The yellowish solution was transferred to a separating funnel with ethyl acetate (70 ml) and repeatedly washed with water (4×35 ml) followed by brine (2×15 ml). The organic phase was dried (Na$_2$SO$_4$) and evaporated to leave 2.64 g of an oil. The residue was purified by column chromatography on silicagel (4? ether in petroleum ether as eluant) to give 2.04 g (76.4%)

of the pure title compound, mp 90–91° C., identical in every respect with the compound prepared in Example 7A.

EXAMPLE 9

3β-Hydroxyfusida-17 (20)Z,24-diene

To a stirred solution of 3-oxofusida-17(20)Z,24-diene (2.88 g, 7.0 mmol) in tetrahydrofuran (50 ml) was added solid sodium borohydride (0.32 g, 8.4 mmol) and, dropwise over 10 minutes, methanol (25 ml). After stirring for a further 15 minutes, the mixture was transferred to a separating funnel with ethyl acetate (150 ml), washed with water (4×50 ml), followed by brine (20 ml) dried ($Na_2SO_4$) and evaporated. The residue was purified by flash chromatography on silicagel (20% ether in petroleum ether) to give after evaporation and crystallization from ether-methanol, 1.44 g (49.8%) of the title compound, mp 123–124° C., $[a]_D^{20}$+ 22.1° (c0.5, $CHCl_3$)

Anal. Calculated for $C_{29}H_{48}O$: C, 84.40; H, 11.72. Found: C, 84.39; H, 11.76.

$^1$H NMR δ 0.76 (s,3H), 0.90 (s,3H), 0.95 (d,3H), 1.09 (s,3H), 1.58 (m,3H), 1.60 (s,3H), 1.65 (s,3H), 1.00–1.75 (m,15H), 1.75–2.38 (m,10H), 3.09 (m,1H), 5.11 (m,1H)

EXAMPLE 10

4-Epi-3β-hydroxyfusida-17(20)Z,24-diene

By following the procedure described in Example 9 and substituting 4-epi-3-oxofusida-17(20)Z,24-diene for the 3-oxofusida-17(20)Z,24-diene, 4-epi-3β-hydroxyfusida-17 (20)Z,24-diene, mp 105–106° C., $[a]_D^{20}$+9.00 (c0.5, $CHCl_3$), was prepared.

$^1$H NMR δ 0.76 (s,3H), 0.89 (d,3H), 0.92 (s,3H), 1.12 (s,3H), 1.58 (m,3H), 1.60 (s,3H), 1.68 (s,3H), 1.02–2.35 (m,25H), 3.79 (m,1H), 5.11 (m,1H)

EXAMPLES 11–16

Protost-17(20)Z-ene Derivatives 24,25-Dihydro derivatives of the compounds described in Examples 1, 2, 3, 4A, 4B and S were obtained by the following procedure: To a solution of the corresponding protosta-17(20)Z,24-diene (10 mmol) in ethanol (50 ml) was added 10% palladium on calcium carbonate catalyst (500 mg), and the mixture was shaken in a hydrogen atmosphere until the consumption of hydrogen ceased (about 30 minutes). The catalyst was filtered off, washed with ethanol, and the combined filtrate and washings were evaporated to dryness. The residue was purified by crystallization or chromatography, and the pure compound thus obtained was characterized.

The following compounds were prepared by the above procedure.

| Example | Name<br>mp (° C.)<br>$^1$H NMR data (δ values) | Formula | Elemental analysis |
|---|---|---|---|
| 11 | 3β-Hydroxyprotost-17(20) Z-en-29-oic Acid<br>163–166 | $C_{30}H_{50}O$ | Calcd.: C 78.55, H 10.99<br>Found: C 78.39, H 10.97 |
| | 0.77 (s, 3H), 0.87 (d, 6H), 0.91 (s, 3H), 1.12 (s, 3H), 1.45 (s, 3H), 1.58 (s, 3H), 1.05–2.38 (m, 27H), 3.18 (dd, 1H) | | |
| 12 | Methyl 3β-hydroxyprotost-17(20) Z-en-29-oate<br>83–84 | $C_{31}H_{52}O_3$ | Calcd.: C 78.76, H 11.09<br>Found: C 78.78, H 11.14 |
| | 0.76 ( s, 3H), 0.79 (s, 3H), 0.87 (d, 6H), 1.12 (s, 3H), 1.39 (s, 3H), 1.56 (bs, 3H), 1.05–2.35 | | |
| 13 | 3β,29-Dihydroxyprotost-17(20) Z-ene<br>119–120 | $C_{30}H_{52}O_2$, $0.5H_2O$ | Calcd.: C 79.41, H 11.77<br>Found: C 79.38, H 11.63 |
| | 0.74 (s, 3H), 0.87 (d, 6H), 0.90 (s, 3H), 1.12 (s, 3H), 1.22 (s, 3H), 1.56 (m, 3H), 1.05–2.37 (m, 26H), 2.45–2.75 (m, 2H), 3.29 (d, 1H), 3.46 (dd, 1H), 4.22 (d, 1H) | | |
| 14 | 3β,29-Dihydroxyprotost-17(20) Z-ene, 3β,29-Ditosylate<br>103–106 | $C_{44}H_{64}6_2S_2$ | Calcd.: C 70.17, H 8.57, S 8.51<br>Found: C 70.17, H 8.67, S 8.50 |
| 15 | 3β,29-Dihydroxyprotost-17(20) Z-ene, 3β,29-Monotosylate<br>129–132 | $C_{37}H_{58}O_4S$ | Calcd.: C 74.20, H 9.76, S 5.35<br>Found: C 74.16, H 9.80, S 5.39 |
| 16 | 3β-Hydroxyprotost-17(20) Z-ene<br>Cryst. | $C_{30}H_{52}O$ | Calcd.: C 84.04, H 12.22<br>Found: C 83.72, H 12.30 |
| | 0.76 (s, 3H), 0.79 (s, 3H), 0.87 (d, 6H), 0.94 (s, 3H), 0.99 (s, 3H), 1.13 (s, 3H), 1.57 (m, 3H), 1.05–1.80 (m, 20H), 1.87–2.38 (m, 7H), 3.25 (dd, 1H) | | |

EXAMPLE 17

Methyl 3β-Tosyloxycrotosta-17(20)Z,24-dien-21-oate

To an icecold solution of methyl 3β-hydroxyprotosta-17 (20)Z,24-dien-21-oate (4.71 g, 10 mmol) in pyridine (25 ml) was added 4-dimethylaminopyridine (DMAP; 0.24 g, 2 mmol) and p-toluenesulfonyl chloride (3.81 g, 20 mmol), and the mixture was stirred at 0–5° C. for another hour before kept at room temperature overnight. After addition of methanol (6 ml), the mixture was stirred for 30 minutes, diluted with ethyl acetate (250 ml), washed with 2 N hydrochloric acid (160 ml), water (2×50 ml) and brine (20 ml), dried ($MgSO_4$) and evaporated. The residual solid (6.16 g) was crystallized from dichloromethane—ethyl acetate to give 5.62 g (89.9%) of the title compound, mp 162–164° C. Recrystallization from dichloromethane—ether afforded the analytical sample, mp 164–165° C.

Anal. Calculated for $C_{38}H_{56}O_5S$: C, 73.03; H, 9.03; S, 5.13. Found: C, 73.07; H, 9.00; S 5.15.

$^1$H NMR δ 0.74 (s,3H), 0.77 (s,3H), 1.11 (s,3H), 1.26 (s,3H), 1.58 (s,3H), 1.59 (s,3H), 1.67 (s, 3H), 2.44 (s,3H), 1.10–2.45 (m,23H), 3.61 (s,3H), 4.29 (dd,1H), 5.09 (m,1H), 7.32 (d,2H), 7.82 (d,2H)

EXAMPLE 18

Methyl Protosta-2,17(20)Z,24-trien-29-oate

To a solution of methyl 3β-hydroxyprotosta-17(20)Z,-24-dien-21-oate (4.72 g, 10 mmol) in pyridine (50 ml) was added at 0–5° C. triflic anhydride (2.4E ml, 15 mmol), and the mixture was stirred at the low temperature for 2 hours before kept in the refrigerator overnight. After addition of methanol (10 ml), the mixture was stirred for 15 minutes, diluted with ethyl acetate (250 ml), washed with 2 N hydrochloric acid (320 ml), water (2×50 ml) and brine (20 ml), dried (MgSO4) and evaporated. The residual oil was purified by column chromatography on silica gel eluting with 5% ether in petroleum ether to give 3.06 g (67.6%) of the title compound, mp 107–108° C. (from ether-methanol).

Anal. Calculated for $C_{31}H_{48}O_2$: C, 82.24; H, 10.69. Found: C, 82.43; H, 10.75.

$^1$H NMR δ 0.78 (s,6H), 1.09 (s,3H), 1.28 (s,3H), 1.58 (bs,3H), 1.60 (s,3H), 1.68 (s,3H), 1.10–2.38 (m,21H), 3.62 (s,3H), 5.11 (m,1H), 5.65 (m,2H)

EXAMPLE 19

9-Hydroxyprotosta-2,17(20)Z,24-triene

A. From Methyl 3β-Tosyloxyorotosta-17(20)Z,24-dien-21-oate

Lithium aluminium hydride (0.38 g, 10 mmol) was dissolved in ether (40 ml) in a two-necked 250 ml round-bottom flask equipped with a reflux condenser and a dropping funnel, and a solution of methyl 3β-tosyloxyprotosta-17(20)Z,24-dien-21-oate (3.0 g, 4.8 mmol) in tetrahydrofuran-ether 1:1 (40 ml) was added dropwise with stirring. After the addition was finished (15 minutes), the mixture was refluxed for 4 hours, and then cooled to room temperature. Ethyl acetate (15 ml) and 2 N sulfuric acid (15 ml) were added, and the mixture was filtered through a celite pad. The aqueous layer was separated, and the organic phase was washed with water (2×15 ml) and brine (10 ml), dried ($Na_2SO_4$) and evaporated. The residual oil was subjected to column chromatography on silica gel eluting with 10% ether in petroleum ether to give 1.16 g (57.0%) of the pure title compound, mp 95-970C (from ether-methanol).

$^1$H NMR δ 0.77 (s,3H), 0.94 (s,3H), 1.10 (s,3H), 1.12 (s,3H), 1.58 (bs,3H), 1.59 (s,3H), 1.69 (s,3H), 1.05–2.40 (m,22H), 3.52 (d,1H), 3.82 (d,1H), 5.11 (m,1H), 5.60 (m,2H)

B. From Methyl Protosta-2,17(20) Z24-trien-29-oate

In a two-necked 250 ml round-bottom flask equipped with a reflux condenser and a dropping funnel, lithium aluminium hydride (0.28 g, 7.5 mmol) was dissolved in dry ether (30 ml), and a solution of methyl protosta-2,17(20)Z,24-trien-29-oate (1.36 g, 3 mmol) in dry ether (30 ml) was added dropwise with stirring. After the addition was finished, the mixture was stirred for a further 30 minutes and then refluxed for two hours. Excess reagent was removed by addition of ethyl acetate (20 ml) and 1 N sulfuric acid (20 ml). After filtration through a celite pad, the filtrate was transferred to a separating funnel. The aqueous layer was extracted with ethyl acetate (20 ml), and the combined organic phases were washed with water (2×10 ml) and brine (10 ml), dried ($MgSO_4$), and evaporated to leave 1.33 g of an oily residue which was purified by column chromatography on silica gel. Elution with 20% ethyl acetate in petroleum ether gave 1.12 g of the pure title compound which was crystallized from ether-hexane, mp 95–97° C.

Anal. Calculated for $C_{30}H_{48}O$, 0.5 $H_2O$: C, 83.08; H, 11.39. Found: C, 82.95; H, 11.14.

EXAMPLE 20

Protosta-2,17(20)Z,24-triene

To an icecold solution of 3β-hydroxyprotosta-17(20)Z,24-diene (1.28 g, 3 mmol) in pyridine (15 ml) was added triflic anhydride (0.74 ml, 4.5 mmol), and the mixture was stirred at 0–5° C. for two hours and then kept in the refrigerator overnight. Methanol (3 ml) was added, and the mixture was stirred for 15 minutes, diluted with ethyl acetate (100 ml), washed with 2 N hydrochloric acid (100 ml), water (2×20 ml) and brine (10 ml), dried (MgSO4), and evaporated to leave an orange oil. Purification by column chromatography on silica gel (eluent: petroleum ether) gave 0.84 g (68.5%) of the title compound, mp 92–94° C. (from ether-methanol).

Anal. Calculated for $C_{30}H_{48}$: C, 88.16; H, 11.84. Found: C, 88.08; H, 11.76.

$^1$H NMR δ 0.78 (s,3H), 0.90 (s,3H), 0.92 (s,3H), 0.94 (s,3H), 1.11 (s,3H), 1.58 (bs,3H), 159 (s,3H), 1.69 (s,3H), 1.10–2.40 (m,21H), 5.12 (m,1H), 5.44 (m,2H)

EXAMPLE 21

Epoxidation of 3β-Hydroxyprotosta-17(20)Z,24-diene

To a stirred solution of 3β-hydroxyprotosta-17(20)Z,24-diene (2.56 g, 6 mmol) in dichloromethane (30 ml) was added dropwise at 0–5° C. 80% m-chloroperbenzoic acid (1.29 g, 6 mmol) dissolved in dichloromethane (30 ml). After the addition was finished (15 minutes), the mixture was stirred at room temperature for another 30 minutes and evaporated. The residue was redissolved in ether (60 ml), and washed with 0.5 M sodium hydrogen carbonate (6×15 ml) and water (2×10 ml), dried ($MgSO_4$), end evaporated to give 2.78 g of a colourless foam which, in addition to minor amounts of the starting material, consisted of four more polar compounds, as revealed by TLC (petroleum ether-ethyl acetate 70:30; Rf values given below). These could be separated by column chromatography on silica gel eluting with 5% to 20% ethyl acetate in petroleum ether.

A. 17β,20β-Eyoxy-3β-hydroxyprotost-24-ene

Yield: 0.91 g (34.2%); crystals from ether-hexane, mp 113–115° C.; Rf 0.42.

$^1$H NMR δ 0.79 (s, 3H), 0.93 (s, 3H), 0.99 (s,3H), 1.01 (s,3H), 1.13 (s,3H), 1.23 (s,3H), 1.62 (bs, 3H), 1.69 (bs,3H), 1.10–1.80 (m,19H), 1.90–2.15 (m, 5H), 3,24 (m,1H) 5.10 (m, 1H)

B. 17α,20α-Epoxy-3β-hydroxyprotost-24-ene

Yield: 1.07 g (40.3%); crystals from ether-hexane, mp 110–112° C.; Rf 0.32.

$^1$H NMR δ 0.79 (s,3H), 0.89 (s,3H), 0.93 (s,3H), 0.99 (s,3H), 1.15 (s,3H), 1.22 (s,3H), 1.62 (bs,3H), 1.69 (bs,3H), 0.75-2.35 (m,24H), 3.24 (dd,1H), 5.09 (m,1H)

C. 17β,20β; 24,25-Diepoxy-3β-hydroxyprotostane

Yield: 0.24 g (8.7%); crystals from ether-hexane, mp 89–95° C.; Rf 0.22.

$^1$H NMR 6 0.79 (s,3H), 0.93 (s,3H), 0.99 (s,3H), 1.01 (s,3H), 1.12 (s,3H), 1.23–1.25 (s,3H), 1.28 (s,3H), 1.32 (s,3H), 1.10–2.10 (m,24H), 2.71 (m,1H), 3,24 (dd,1H)

D. 17α,20α; 24,25-Diepoxy-3β-hydroxyprotostane

Yield: 0.17 g (6.2%); crystals from ether-hexane, mp 134–140° C.; Rf 0.16.

$^1$H NMR δ 0.80 (s,3H), 0.88 (s,3H), 0.93–0.94 (s,3H), 0.99 (s,3H), 1.16 (s,3H), 1.21–1.23 (s,3H), 1.29 (s,3H), 1.32 (s,3H), 1.10–2.07 (m,23H), 2.29 (dd,1H), 2.72 (t,1H), 3.25 (dd,1H)

EXAMPLE 22

Epoxidation of Methyl 3β-Hydroxyprotosta-17(20) Z24-dien-29-oate

By following the procedure described in Example 21 but substituting 3β-hydroxyprotosta-17(20)Z,24-dien-29-oate for the 3β-hydroxyprotosta-17(20)Z,24-diene, the following five epoxy derivatives were prepared and separated by column chromatography on silica gel eluting with 10% to 60% ether in petroleum ether. Rf values of the new compounds, as determined by TLC in petroleum ether—ether 40:60, are given below.

A. Methyl 17β,20β-Epoxy-3β-hydroxyprotost-24-en-29-oate

Yield: 1.70 g (34.9%); crystals from ether, mp 149–152° C.; Rf 0.46.

$^1$H NMR δ 0.78 (s,3H), 1.01 (s,3H), 1.12 (s,3H), 1.23 (s,3H), 1.39 (s,3H), 1.62 (bs,3H), 1.69 (bs,3H), 1.10–2.15 (m,23H), 3.10 (m,1H), 3.65 (s,3H), 3.73 (d,1H), 5.09 (m,1H)

B. Methyl 24,25-Epoxy-3β-hydroxyprotost-17(20)Z-en-29-oate

Yield: 0.50 g (10.3%); colourless foam; Rf 0.40.

$^1$H NMR δ 0.79 (s,3H), 1.10 (s,3H), 1.14 (dd,1H), 1.30 (s,3H), 1.42 (s,3H), 1.59 (m,3H), 1.61 (bs,3H), 1.69 (bs,3H), 1.20–1.75 (m,11H), 1.85–2.27 (m,10H), 2.30 (bd,1H), 4.12 (d,1H, J=6.1 Hz), 4.42 (d,1H, J=6.1 Hz), 4.65 (dd,1H), 5.12 (m,1H)

C. Methyl 17α,20α-Epoxy-3β-hydroxypratost-24-en-29-oate

Yield: 1.26 g (25.9%); colourless foam; Rf 0.36.

$^1$H NMR δ 0.78 (s,3H), 0.90 (s,3H), 1.15 (s,3H), 1.22 (s,3H), 1.40 (s,3H), 1.62 (bs,3H), 1.69 (bs,3H), 1.10–2.30 (m,23H), 3.10 (m,1H), 3.65 (s,3H), 3.70 (d,1H), 5.08 (m,1H)

D. Methyl 17β,20β;24,25-Diepoxy-3β-hydroxyprotostan-29-oate

Yield: 0.45 g (9.0%); crystals from ether, mp 185–188° C.; Rf 0.28.

$^1$H NMR δ 0.78 (s,3H), 1.01 (s,3H), 1.11 (s,3H), 1.25 (s,3H), 1.27 (s,3H), 1.32 (s,3H), 1.39 (s,3H), 1.10–2.06 (m,23H), 2.71 (m,1H), 3.10 (m,1H), 3.65 (s,3H), 3.73 (d,1H)

E. Methyl 17α,20α;24,25-Diepoxy-3β-hydroxyprotostan-29-oate

Yield: 0.29 g (5.80); colourless foam; Rf 0.19

$^1$H NMR δ 0.78 (s,3H), 0.88 (s,3H), 1.15 (s,3H), 1.22 (s,3H), 1.28 (s,3H), 1.32 (s,3H), 1.40 (s,3H), 1.15–2.05 (m,22H), 2.27 (m,1H), 2.71 (t,1H), 3.11 (m,1H), 3.65 (s,3H), 3.72 (d,1H)

EXAMPLE 23

3β-Mesyloxyprotosta-17 (20)Z,24-diene

To an icecold solution of 3β-hydroxyprotosta-17(20)Z, 24-diene (0.43 g, 1.0 mmol) in pyridine (25 ml) was added methanesulfonyl chloride (0.26 ml, 1.5 mmol) with stirring. The mixture was stirred at 0–5° C. for one hour and then kept in the refrigerator overnight. After addition of methanol (0.15 ml) and stirring for 10 minutes at 0–5° C., the mixture was poured onto icecold water (5 ml). Ethyl acetate (10 ml) and 4 N aqueous hydrochloric acid (10 ml) were added with stirring, and the mixture was transferred to a separating funnel. The aqueous layer (pH 2) was separated and the organic phase washed with water (2×5 ml) and brine (5 ml), dried (MgSO$_4$) and evaporated. The resulting oil was crystallized from ether-hexane to give 0.39 g (77.3%) of the title compound, mp 99–102° C.

$^1$H NMR δ 0.75 (s,3H), 0.87 (s,3H), 0.97 (s,3H), 1.03 (s,3H), 1.12 (s,3H), 1.58 (m,3H), 1.50 (bs, 3H), 1.68 (bs, 3H), 1.05–2.37 (m,23H), 3.02 (s,3H), 4.37 (dd,1H), 5.11 (m,1H)

EXAMPLE 24

3β,29-Epoxyprotosta-17(20)Z,24-diene

To a stirred solution of 39,29-dihydroxyprotosta-17(20) Z,24-diene,29-monotosylate (0.60 g, 1.0 mmol) in dry tetrahydrofuran (8 ml) was added dropwise (5 minutes) 1 M lithium triethylhydroborate in tetrahydrofuran (4 ml), and the mixture was stirred for 45 minutes. A few drops of water, followed by 2 N sodium hydroxide (2 ml). and 30% aqueous hydrogen peroxide, were added, and the mixture was stirred for a further 30 minutes. After addition of water (20 ml), the product was extracted with ethyl acetate (20+10 ml). The combined organic phases were washed with water (2×5 ml) and brine (10 ml), dried (YgSO$_4$) and evaporated. The residual oil was purified by column chromatography on silica gel (eluting with 5i ethyl acetate in petroleum ether) to afford 0.38 g (89.5%) of the title compound which was crystallized from ether-methanol, mp 83–85° C.

$^1$H NMR δ 0.79 (s,3H), 1.10 (s,3H), 1.14 (dd,1H), 1.30 (s,3H), 1.42 (s,3H), 1.59 (m,3H), 1.61 (bs,3H), 1.69 (bs,3H), 1.20–1.75 (m,11H), 1.85–2.27 (m,10H), 2.30 (bd,1H), 4.12 (d,1H, J=6.1 Hz), 4.42 (d,1H, J=6.1 Hz), 4.65 (dd,1H), 5.12 (m,1H)

EIMS: calcd for $C_{30}H_{48}O$ (M$^+$) 424.4, found 424.3

EXAMPLE 25

3β,20(R)-Dihvdroxyorotosta-16,24-diene

A. From 17β,20β-Epoxy-3β-hydroxyprotost-24-ene by Lithium Aluminium Hydride Treatment/Acid Hydrolysis.

17β,20β-Epoxy-3β-hydroxyprotost-24-ene (111 mg, 0.25 mmol) was added to a solution of lithium aluminium hydride (57 mg, 1.50 mmol) in dry ether (5 ml), and the mixture was refluxed for 3.5 hours. Ethyl acetate (5 ml) and 2 N sulfuric acid (2.5 ml) were added, and the mixture was kept at room temperature for 2 days. The aqueous layer was separated and extracted with ethyl acetate (5 ml), and the combined organic phases were washed with 1 M sodium hydrogen carbonate (2×5 ml), water (2×5 mL) and brine (5 ml), dried (MgSO$_4$) and evaporated. The oily residue (106 mg) was purified by column chromatography on silica gel (eluting with 15% to 25% ethyl acetate in pentane) to afford 15 mg (13.6%) of the desired compound as a colourless oil.

$^1$H NMR δ 0.79 (s,3H), 1.10 (s,3H), 1.14 (dd,1H), 1.30 (s,3H), 1.42 (s,3H), 1.59 (m,3H), 1.61 (bs, 3H), 1.69 (bs, 3H), 1.20–1.75 (m,11H), 1.85–2.27 (m,10 H), 2.30 (bd,1H), 4.12 (d,1H, J=6.1 Hz), 4.42 (d,1H, J=6.1 Hz), 4.65 (dd,1H), 5.12 (m,1H)

EIMS: calcd for $C_{30}H_{48}O$ (M$^+$-H$_2$O) 424.3705, found 424.356.

B. From 17β,20β-Epoxy-3β-hydroxyprotost-24-ene by Treatment with Aluminium Chloride A solution of 17β,20-epoxy-3β-hydroxyprotost-24-ene (0.44 g, 1.0 mmol) and triethylamine (0.21 ml, 1.5 mmol) in dry tetrahydrofuran (8 ml) added to a dried 50 ml 2-necked round-bottomed flask equipped with a magnetic stirring bar and a septum cap. The flask was cooled to 0° C., 0.375 M aluminium chloride (anhydrous) in dry tetrahydrofuran (2 ml, 0.75 mmol) was added by syringe, and the mixture was stirred for 10 minutes at 0–5° C. and then for 5 hours at room temperature. The reaction mixture was poured into cold water (40 ml), and the product was extracted with ethyl acetate (2×20 ml). The combined organic extracts were washed with water (2×10 ml) and brine (10 ml), dried (MgSO$_4$) and evaporated to yield 0.58 g of the crude product. Crystallization from ether-hexane gave 0.33 g (77.7%) of the pure compound, mp 151–154° C.

EXAMPLE 26

3β,20(S)-Dihydroxyprotosta-16,24-diene

17β,20-Epoxy-3β-hydroxyprotost-24-ene (221 mg, 0.5 mmol) and triethylamine (0.105 ml, 0.75 mmol) were dissolved in dry tetrahydrofuran (4 ml) in a dried 10 ml 2-necked round-bottomed flask equipped with a magnetic stirring bar and a septum inlet. After establishing an argon atmosphere, the flask was cooled to 0C, and 0.375 M aluminium chloride (anhydrous) in dry tetrahydrofuran (0.4 ml, 0.15 mmol) was added by syringe with stirring. The reaction was stirred for 5 minutes at 0–5° C. and then for 42 hours at room temperature. The mixture was poured into icecold water (25 ml) and extracted with ethyl acetate (20+10 ml), and the combined organic phases were washed with water (2×10 ml) and brine (10 ml), dried (MgSO$_4$) and evaporated to afford 232 mg of crude product. Purification by column chromatography on silica gel eluting with 15% to 250 of ethyl acetate in petroleum ether gave, in addition to 106 mg of unreacted starting material, 68 mg (30.7i) of the title compound which was crystallized from ether-hexane, mp 122–128° C.

$^1$H NMR δ 0.79 (s,3H), 0.92 (s,3H), 0.99 (s,6H), 1.19 (s,3H), 1.28 (s,3H), 1.60 (bs, 3H), 1.68 (bs,3H), 1.00–2.00

(m,21H), 2.22 (bd,1H), 2.71 (m,1H), 3.23 (dd,1H), 5.11 (m,1H), 5.44 (m,1H)

EIMS: calcd for $C_{30}H_{48}O$ ($M^+$-$H_2O$) 424.3705, found 424.36

EXAMPLE 27
3β,20,24-Trihydroxyprotostane

3β-Hydroxyprotosta-17(20)Z,24—diene (427 mg, 1.0 mmol) was dissolved in dry tetrahydrofuran (10 ml) in a dried 50 ml round-bottomed flask equipped with a magnetic stirring bar and a septum cap. After establishing an argon atmosphere, the stirred solution was cooled to 0° C. and 1 M borane in tetrahydrofuran (12 ml) was added by syringe. The mixture was stirred for 5 minutes at 0–5° C. and for 18 hours at room temperature. The flask was cooled to 0° C., and water (1 ml) was added, followed by 2 N sodium hydroxide (12 ml) and 30% hydrogen peroxide (3.6 ml). After stirring for 1 hour at room temperature, the reaction mixture was poured into water (40 ml) and extracted with ethyl acetate (2×25 ml). The combined organic extracts were washed with water (4×10 ml) and brine (20 ml), dried ($MgSO_4$) and evaporated to yield 580 mg of a solid residue. Purification by column chromatography on silica gel (50% ethyl acetate in petroleum ether as eluant) gave 110 mg of a less polar product (A), characterized as a 4:1 mixture of two diastereomeric 3β,20,24-trihydroxyprotostanes, and 302 mg of a more polar product (B) representing an approximate 2:1 mixture of two other 3,20,24-trihydroxyprotostane diastereomers. The latter was crystallized from ether, mp 179–182° C.

Product (A)

$^1$H NMR: (A) δ 0.78 (s,3H), 0.91 (s,6H), 0.92 (d,6H), 0.98 (s,3H), 1.09 (s,3H), 1.21 (s,3H), 1.05–2.20 (m,28H), 3.23 (dd,1H), 3.33 (m,1H)

EIMS: calcd for $C_{30}H_{50}O$ ($M^+$-$2H_2O$) 426.3862, found 426.38

Product (B)

$^1$H NMR: (B) δ 0.78 (s,3H), 0.83 (s,3H), 0.92 (s,3H), 0.92 (d,6H), 0.98 (s,3H), 1.11 (s,3H), 1.13 (s,3H), 1.10–2.00 (m,28H), 3.24 (dd,1H), 3.32 (m,1H)

EIMS: calcd for $C_{30}H_{50}O$ ($M^+$-$2H_2O$) 426.3862, found 426.28

EXAMPLE 28
3β,17-Dihydroxyprotostane

3β-Hydoxyprotost-17(20)Z-ene (429 mg, 1.0 mmol) was added to a dried 50 ml round-bottomed flask equipped with a stirring bar and a septum cap and connected to an argon/vacuum line. The flask was evacuated and filled with argon, and dry tetrahydrofuran (10 ml) was added. The stirred solution was cooled to 0° C., and 1 M borane in tetrahydrofuran (6 ml) was added by syringe. The reaction was stirred for 5 minutes at 0° C. and then for 18 hours at room temperature. The flask was cooled to 0–5° C., and water (1 ml) was added with stirring, followed by 2 N sodium hydroxide (6 ml) and 30% hydrogen peroxide (1.8 ml). After stirring for 1 hour at room temperature, the reaction mixture was transferred to a separating funnel, diluted with water (40 ml) and extracted with ethyl acetate (2×25 ml). The combined organic extracts were washed with water (2×20 ml) and brine (20 ml), dried ($MgSO_4$) and evaporated to give 486 mg of a solid product. The residue was subjected to column chromatography on silica gel eluting with 15% to 25k ethyl acetate in petroleum ether to give, in addition to 221 mg of unreacted starting material, 75 mg of the title compound which crystallized from ether-hexane, mp 147–150° C.

$^1$H NMR δ 0.79 (s,3H), 0.83 (s,3H), 0.87 (d,3H), 0.87 (d,3H), 0.91 (s,3H), 0.96 (s,3H), 0.98 (s,3H), 1.16 (s,3H), 1.00–2.00 (m,29H), 3.25 (dd,1H)

EIMS: calcd for $C_{30}H_{52}O$ ($M^+$-$H_2O$) 428.4018, found 428.30

What we claim is:

1. A compound selected from the group consisting of (a) 17β,20β-Epoxy-3β-hydroxyprotost-24-ene, (b) 17α,20α-Epoxy-3β-hydroxyprotost-24-ene, (c) 17β,20β;24,25-Diepoxy-3β-hydroxyprotost,ane, (d) 17α,20α;24,25-Diepoxy-3β-hydroxyprotostane, (e) Methyl 24,25-Epoxy-3β-hydroxyprotost-17(20)Z-en-29-oate, (f) 363,29-Epoxyprotosta-1 7(20)Z,24-diene, (g) 3β,20,24-Trihydroxyprotostane, (h) 3β-Hydroxyprotosta-17(20)Z,24-dien-29-oic acid and its salts and esters.

2. A compound having the formula I

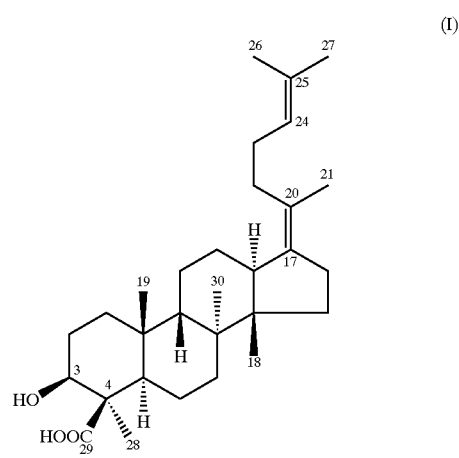

(I)

or salts or esters thereof.

3. A pharmaceutical composition comprising at least one compound selected from the group consisting of a) 17β,20β-Epoxy-3β-hydroxyprotost-24-ene, b) 17α,20α-Epoxy-3β-hydroxyprotost-24-ene, c) 17β,20β; 24,25-Diepoxy-3β-hydroxyprotostane, d) 17α,20α; 24,25-Diepoxy-31β-hydroxyprotostane, e) Methyl 24,25-Epoxy-3β-hydroxyprotost-17(20)Z-en-29-oate, f) 3β,29-Epoxyprotosta-17(20)Z,24-diene, g) 3β,20,24-Trihydroxyprotostane, h) 3β-Hydroxyprotosta-17(20)Z,24-dien-29-oic acid and pharmaceutically acceptable salts and esters thereof, together with a pharmaceutically acceptable, non-toxic carrier therefor.

4. A method of lowering cholesterol in a patient in need of such treatment which comprises administering to said patient a compound of Formula (II):

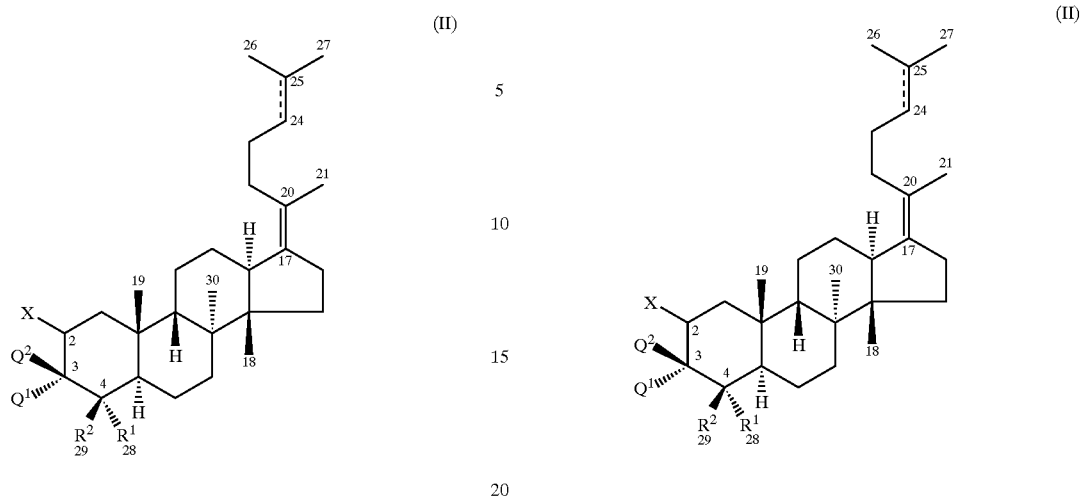

wherein $R^1$ stands for hydrogen or methyl;

$R^2$ is hydrogen, methyl, $CH_2OH$, $CH_2OR^3$, CHO, $CH=CH_2$, COOH or $COOR^4$;

$R^3$ stands for straight or branched ($C_1$–$C_6$) alkyl, aralkyl or aryl, optionally substituted with halogen, hydroxy or carboxy; alkanesulfonyl or arenesulfonyl; ($C_1$–$C_4$) alkanoyl or aroyl, optionally substituted with halogen, hydroxy or carboxy;

$R^4$ stands for straight or branched ($C_1$–$C_6$)alkyl, ($C_2$–CE) alkenyl, ($C_2$–$C_6$)alkynyl, aralkyl, aryl, alkanoyloxy-alkyl or dialkylaminoethyl;

$Q^1$ and $Q^2$ are each independently hydrogen, hydroxy or a group $OR^3$; or, taken together, $Q^1$ and $Q^2$ stand for oxygen; or $Q^1$ ($Q^2$) and $R^1$ ($R^2$), when taken together, constitute a double bond that connects carbon atoms 3 and 4; or $Q^2$ and $R^2$, when taken together with carbon atoms 3 and 4, may form an oxetane ring;

X is hydrogen; or X and $Q^1$, ($Q^2$) when taken together, form a double bond connecting carbon atoms 2 and 3;

the C24,25-bond is a double bond or a single bond;

and, additionally, one or more of the double bonds connecting carbon atoms 2 and 3, 3 and 4, 17 and 20, and/or 24 and 25 may optionally be epoxidized with formation of an oxirane ring or hydrated to give a carbon—carbon single bond where one of the carbon atoms is substituted with hydroxy, a pharmaceutically acceptable salt thereof or an in vivo hydrolysable ester thereof.

5. A method of treating atherosclerosis which comprises administering to a human in need of such treatment an effective amount of a compound of Formula (II)

wherein $R^1$ stands for hydrogen or methyl;

$R^2$ is hydrogen, methyl, $CH_2OH$, $CH_2OR^3$, CHO, $CH=CH_2$, COOH or $COOR^4$;

$R^3$ stands for straight or branched ($C_1$—$C_6$) alkyl, aralkyl or aryl, optionally substituted with halogen, hydroxy or carboxy; alkanesulfonyl or arenesulfonyl; ($C_1$–$C_4$) alkanoyl or aroyl, optionally substituted with halogen, hydroxy or carboxy;

$R^4$ stands for straight or branched ($C_1$–$C_6$)alkyl, ($C_2$–$C_3$,) alkenyl, ($C_2$–$C_6$)alkynyl, aralkyl, aryl, alkanoyloxy-alkyl or dialkylaminoethyl;

$Q^1$ and $Q^2$ are each independently hydrogen, hydroxy or a group $OR^3$; or, taken together, $Q^1$ and $Q^2$ stand for oxygen; or $Q^1$ ($Q^2$) and $R^1$ ($R^2$), when taken together, constitute a double bond that connects carbon atoms 3 and 4; or $Q^2$ and $R^2$, when taken together with carbon atoms 3 and .4, may form an oxetane ring;

X is hydrogen; or X and $Q^1$, ($Q^2$) when taken together, form a double bond connecting carbon atoms 2 and 3;

the C24,25-bond is a double bond or a single bond;

and, additionally, one or more of the double bonds connecting carbon atoms 2 and 3, 3 and 4, 17 and 20, and/or 24 and 25 may optionally be epoxidized with formation of an oxirane ring or hydrated to give a carbon—carbon single bond where one of the carbon atoms is substituted with hydroxy, a pharmaceutically acceptable salt thereof or an in vivo hydrolysable ester thereof.

6. A method for producing a compound according to claim 1 in which a) an alkyl ester of formula I is reacted with lithium aluminium hydride to form a protostanediol of formula 4;

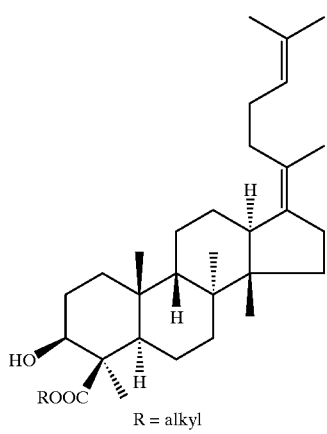

I

R = alkyl b) the compound of formula 4 is treated with id-toluenesulfonyl chloride in the presence of a base to produce a mixture of tosylates of formulas 5a and 5b which were separated;

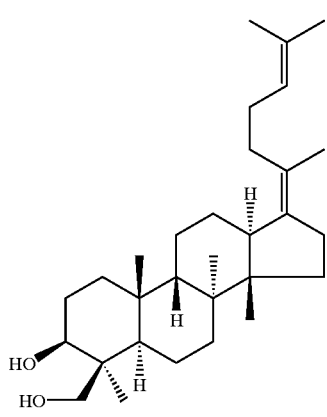

4

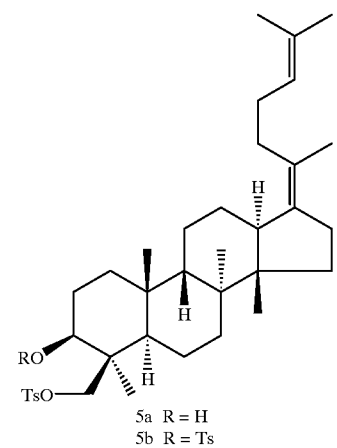

5a R = H
5b R = Ts c) the monotosylate of formula 5a is reduced with lithium aluminium hydride to form a protosterol of formula 6, or with lithium triethylhydroborate to give an oxetane of formula 24;

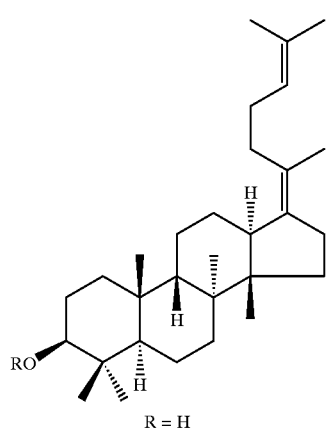

6

R = H

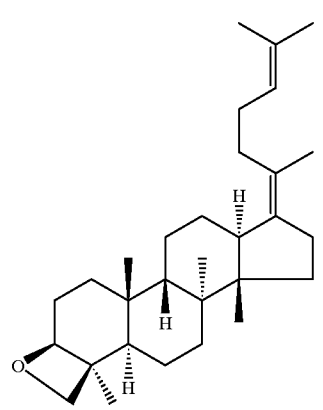

24 d) the compound of formula 6 is treated with an organic peracid to form a mixture of epoxides which is separated to yield the desired 17β,20β- and 17α,20α-epoxy-3β-hydroxyprotost-24-enes in pure form and the corresponding 17β,20β;24,25- and 17α,20α;24,25-diepoxy-3β-hydroxyprotostanes as C24 diastereomeric mixtures;

e) alternatively, the compound of formula 6 is subjected to hydroboration followed by oxidation to form a mixture of diastereomeric 3β,20,24-trihydroxyprotostanes;

f) alternatively, the compound of formula 6 is subjected to oxymercuration followed by demercuration to form a mixture of diastereomeric trihydroxyprotostanes.

7. A method according to claim 6 wherein the base in (b) is pyridine;

the peracid in (d) is m-chloroperbenzoic acid; the hydroboration in (e) is carried out with borane; and the oxymercuration is carried out with mercury (II) acetate.

\* \* \* \* \*